United States Patent [19]
Rupe

[11] Patent Number: 4,855,239
[45] Date of Patent: Aug. 8, 1989

[54] TEST COMPOSITION AND DEVICE FOR THE DETERMINATION OF CYANURIC ACID IN WATER

[75] Inventor: Chauncey O. Rupe, Elkhard, Ind.

[73] Assignee: Environmental Test Systems, Inc., Elkhart, Ind.

[21] Appl. No.: 138,045

[22] Filed: Dec. 28, 1987

[51] Int. Cl.⁴ .................. G01N 33/18; E04H 3/16; E04H 3/20

[52] U.S. Cl. .................. 436/106; 210/169; 422/57

[58] Field of Search .......... 436/106, 98; 210/169; 422/57

[56] References Cited

U.S. PATENT DOCUMENTS

| | | | |
|---|---|---|---|
| 4,039,284 | 8/1977 | Mancini | 436/98 |
| 4,162,897 | 7/1979 | Capuano | 422/106 |
| 4,613,575 | 9/1986 | Westrup et al. | 436/106 |
| 4,670,218 | 6/1987 | Gantzer et al. | 422/56 |
| 4,673,513 | 6/1987 | Powell | 210/169 |

FOREIGN PATENT DOCUMENTS 005595 2/1970 Japan.

OTHER PUBLICATIONS

The Merck Index, Tenth edition 1983.
Downes et al., Water Res 18(3), 1984, pp. 277–280.

*Primary Examiner*—Barry S. Richman
*Assistant Examiner*—Lyle Alfandary-Alexander
*Attorney, Agent, or Firm*—Harry T. Stephenson

[57] ABSTRACT

A colorimetric test reagent composition is presented for determining the amount of cyanuric acid in water. Cyanuric acid is added to outdoor swimming pool water to stabilize the chlorine added as a sanitizer. Basically the test composition utilizes melamine and an indicator material which responds to a change in pH of the test environment caused by the action of cynanuric acid on the reagent composition. Preferably the test composition is incorporated in a porous matrix which results in a convenient solid state test device.

9 Claims, No Drawings

TEST COMPOSITION AND DEVICE FOR THE DETERMINATION OF CYANURIC ACID IN WATER

FIELD OF THE INVENTION

The present invention relates to a test reagent composition for colorimetrically determining the quantity of cyanuric acid in water. More particularly, the invention relates to a test composition which can be incorporated into a matrix such as paper which when contacted with an aqueous fluid containing cyanuric acid will result in the formation of a color which is proportional to the quantity of cyanuric acid present.

BACKGROUND OF THE INVENTION

As the number of swimming pools and spas increases, the need for effective tools to monitor and control pool water chemistry and especially sanitizer levels becomes more and more important. This is especially true in pools used by the public where the bather concentration is high and the threat of contagious diseases is always present. In order to control the harmful microorganism population of pools, it has been found over the years that chlorine is the most effective and economical sanitizer. However, as popular as chlorine is, it nevertheless has certain drawbacks which must be considered. A particularly serious problem associated with the use of chlorine in outdoor pools is that it tends to be destroyed by sunlight.

In this regard it has been found that the addition of cyanuric acid (2,4,6-trihydroxy-1,3,5-triazine) to the outdoor pool water can be effective as an extender or stabilizer for chlorine. However, the concentration must be rather carefully adjusted since too little obviously is ineffective as a stabilizer for the chlorine while too much can dramatically slow down the rate at which microorganisms are destroyed by the chlorine. It has been found that the effective concentration of cyanuric acid lies between 40 and 120 parts per million (ppm).

In order to maintain the effectiveness of the cyanuric acid in the swimming pool, it is necessary to measure the concentration thereof using a test device or concentration measuring system. The current test most commonly used in the swimming pool industry involves the melamine turbidimetric methodology. In this scheme, melamine is added to a sample of the pool water which in the presence of cyanuric acid causes the formation of a finely dispersed precipitate. The turbidity created by this precipitate formation is proportional to the amount of cyanuric acid present. By measuring this turbidity using visual or instrumental schemes, an estimation of the concentration of cyanuric acid can be obtained. This test however is not completely acceptable since turbidimetric methods tend in general to be unreliable in that other factors can cause turbidity and precipitates are obviously less homogenous that solutions.

For this reason, attempts have been made over the years to replace the turbidimetric analytical procedures with colorimetric methodolgies. To date, an acceptable, commercially available colorimetric method for determining cyanuric acid does not exist.

DESCRIPTION OF THE PRIOR ART

U.S. Pat. No. 4,039,284 discloses and claims a formulation for the colorimetric determination of cyanuric acid comprising a thymolsulfonphthalein compound, monoethanolamine and a stilbene compound. Regardless of its suggested efficacy, it appears that there are no commercially available products based on this technology.

Aside from the above patent, very little literature exists relative to the interaction of cyanuric acid with other compounds to form colored compounds. Veneable, C. and Moore, F.; J. Am. Chem. Soc. 39, 1750, 1917 discloses that cyanuric acid will react with certain metals such as copper to produce colored compounds. However, the reaction must take place under severe alkaline conditions and heat which obviously is not amenable to a field test system.

All other prior art literature relates to colorless turbidimetric reactions between cyanuric acid and other compounds which art has no relevance here.

SUMMARY OF THE INVENTION

It has now been unexpectedly found that by using melamine, an appropriate pH indicator material and adjusting the pH of the test composition to within a designated range, a simple to use and effective colorimetric cyanuric acid test system can be devised. Basically, this invention involves the utilization of melamine and a pH indicator, which composition, when contacted with cyanuric acid, causes a shift in the pH of the test system and in effect creates a color change which is proportional to the amount of cyanuric acid in the fluid being tested. Although the melamine/cyanuric acid precipitate can be removed to more easily and accurately determine the color produced when the composition is used as a liquid format, or other means can be employed to read the color formed, it is preferable to incorporate the composition in a solid state matrix such as paper. In this format the interference due to the melamine/cyanuric acid precipitate is eliminated.

DESCRIPTION OF THE PREFERRED EMBODIMENTS

Although the basic reagent composition of the present invention comprises melamine and a pH indicator, two slightly different approaches can be utilized to achieve a useful product. Both approaches involve the adjustment of the pH of the test composition prior to contacting the composition with the fluid being tested. In the first approach, the pH of the composition is adjusted to within a range of from about pH 5 to a pH of less than about 7, whereby contact of the composition with cyanuric acid in the fluid being tested results in neutralization and a corresponding drop in the pH of the test fluid, the pH indicator being responsive to such pH drop to give a visual color change proportional to the amount of cyanuric acid present. In the second approach, the pH of the composition is adjusted to within a range of from about 7 to about 8. In such an approach, the melamine in the reagent composition reacts with cyanuric acid present to cause a change in the equilibrium between the enol and the keto forms of cyanuric acid, resulting in a higher or more basic pH in the test environment, which in the presence of an appropriate pH indicator likewise causes a perceptible color change indicative of the amount of cyanuric acid present in the fluid being tested.

In preparing the compositions of the present invention, consideration must be given to the selection of indicator materials and the concentration of melamine in the test composition. As previously indicated, the test compositions should be adjusted to a pH of either from about 5 to about 7 or from about 7 to about 8. In view of this, the indicator must accordingly be selected to change color when the pH of the test environment either increases or decreases. Indicators such as methyl red, phenol red, thymol blue, bromthymol blue, cresol red, metacresol purple and mixtures thereof may be selected as color forming agents.

The concentration of melamine (cyanurotriamide) in the reagent mixture should be set at from about 0.02 g/100 ml to about 0.5 g/100 ml. The melamine concentration must be set to be in excess of the anticipated concentration of cyanuric acid being detected but must not be such that the pH change caused by contact of the reagent composition with the cyanuric acid is hindered.

It has also unexpectedly been found that the utilization of a thickening agent such polystyrene sulfonic acid or Gantrex is advantageous in that the color response of the test composition to cyanuric acid is enhanced. It is believed that these materials localize the color, making the color response more easily detected.

As previously noted, it is preferable to incorporate the reagent composition into a solid state matrix so that the formation of precipitate does not hinder in the estimation of the color change. Examples of matrix materials which can be utilized are filter paper, glass fibers, cellulosic materials, synthetic fibers, polymers, particulate inorganic materials, and so forth. The matrix must however be impervious to and not react with the fluid being tested and must be reasonably hydrophilic and porous so that the fluid being tested wets the matrix and the analyte contained therein, i. e. cyanuric acid, reacts with the incorporated reagent composition.

A particularly advantageous use of the solid state test devices described next above is in conjunction with an instrumental read out means. This can be accomplished by using a reflectance color measuring device wherein the color of the reagent matrix is measured and interpreted to give a readout in concentration of cyanuric acid in the fluid being tested.

The following Examples are illustrative of the present invention.

EXAMPLE 1.

| | |
|---|---|
| Deionized Water | 95.0 ml. |
| Polystyrene Sulfonic Acid (Na Salt) | 0.5 g. |
| Melamine | 0.1 g. |
| Methyl Red 0.1% in dilute NaOH | 0.5 ml. |

The polystyrene sulfonic acid salt was dissolved in the deionized water with stirring. The melamine was added and the stirring continued until the melamine dissolved. The methyl red was added and the pH of the solution adjusted to 5.25 with HCl. E & D 205 filter paper was dipped into the reagent solution and dried in a hot air tunnel. The resulting dried paper was light pink in color.

Standard solutions of cyanuric acid in swimming pool water were prepared and the following colors obtained by immersing the reagent paper into such standard solutions and immediately removing the paper from the water:

| Cyanuric Acid Conc. (ppm) | Color |
|---|---|
| 0 | Orange |
| 50 | Pink |
| 100 | Red |
| 200 | Dark Red |

EXAMPLE 2

| | |
|---|---|
| Deionized water | 95 ml. |
| Methyl Red 0.1% in dilute NaOH | 3 ml. |
| Gantrez AN119 | 0.1 g. |
| Melamine | 0.2 g. |

The above ingredients were combined as in Example 1, except that the solution was heated to solubilize the Gantrez. The solution was cooled and the pH adjusted to 5.75 with HCl. Reagent papers were prepared as in Example 1 and when contacted with tap water having various concentrations of cyanuric added thereto gave the following results:

| Cyanuric Acid Conc. (ppm) | Color |
|---|---|
| 0 | Orange |
| 50 | Pink |
| 100 | Light Red |
| 250 | Red |
| 500 | Dark Red |

EXAMPLE 3

| | |
|---|---|
| Deionized water | 88 ml. |
| Polyvinyl alcohol | 1.5 g. |
| Surfactant (Igepal CO-660) 0.1% | 10 ml. |
| Phenol red 0.1% (Na salt) | 5 ml. |
| Thymol blue 0.1% (Na salt) | 7 ml |
| Melamine | 0.1 g. |

The above composition was prepared essentially as in Example 2. The pH of the composition was adjusted to 7.5 and the composition impregnated into filter paper and dried. The dried paper was yellow in appearance.

Test strips made from this paper gave the following results when dipped into and immediately removed from tap water containing the indicated amounts of cyanuric acid:

| Cyanuric Acid Conc. (ppm) | Color |
|---|---|
| 0 | Orange |
| 50 | Tangerine |
| 100 | Red |
| 150 | Violet |
| 200 | Purple |

EXAMPLE 4

| | |
|---|---|
| Deionized water | 88 ml. |
| Polystyrene sulfonic acid (Na salt) | 0.3 g. |
| Phenol red 0.1% (Na salt) | 5 ml. |
| Thymol blue 0.1% (Na salt) | 7 ml. |
| Melamine | 0.1 g. |

The reagent composition was prepared and incorporated into filter paper essentially as described in Example 3. The following results were obtained when test strips were contacted with tap water containing the indicated amounts of cyanuric acid.

| Cyanuric Acid Conc. (ppm) | Color |
|---|---|
| 0 | Orange |
| 40 | Pink |
| 80 | Red |
| 160 | Violet |
| 320 | Purple |

What is claimed is:

1. A reagent composition for the determination of cyanuric acid in water comprising melamine and an indicator which changes color in response to a change in the pH of the water due to the presence of cyanuric acid, the composition being adjusted to a pH of from about 5 to about 8.

2. A composition as in claim 1 wherein the pH of the composition is adjusted to a range of from about 5 to about 7.

3. A composition as in claim 1 wherein the pH of the composition is adjusted to a range of from about 7 to about 8.

4. A composition as in claim 1 wherein the indicator is selected from the group consisting of methyl red, phenol red, thymol blue, cresol red, metacresol purple, and mixtures thereof.

5. A test device for estimating the amount of cyanuric acid in water comprising a porous matrix containing the dried residue of a reagent composition adjusted to a pH of from about 5 to about 8, which composition includes melamine and a pH indicator which changes color in response to a change in the pH of the environment in the matrix when the matrix is contacted with an aqueous solution of cyanuric acid.

6. A test device as in claim 5 wherein the reagent composition includes a thickening agent selected from the group consisting of polystyrene sulfonic acid and gantrez.

7. A test device as in claim 5 wherein the pH of the composition is adjusted to a range of from about 5 to about 7.

8. A test device as in claim 5 wherein the pH of the composition is adjusted to a range of from about 7 to about 8.

9. A test device as in claim 5 wherein the pH indicator is selected from the group consisting of methyl red, phenol red, thymol blue, cresol red, metacresol purple and mixtures thereof.

* * * * *